US009682026B2

(12) United States Patent
Kohli et al.

(10) Patent No.: US 9,682,026 B2
(45) Date of Patent: *Jun. 20, 2017

(54) ORAL CARE PRODUCT AND METHODS OF USE AND MANUFACTURE THEREOF

(75) Inventors: Rajnish Kohli, Hillsborough, NJ (US); Richard Scott Robinson, Belle Mead, NJ (US); Sergio Leite, Kendall Park, NJ (US); Eric A. Simon, Somerset, NJ (US); Richard J. Sullivan, Atlantic Highlands, NJ (US); Ralph Peter Santarpia, III, Edison, NJ (US); Michael Prencipe, West Windsor, NJ (US); Ravi Subramanyam, Belle Mead, NJ (US); Sarita V. Mello, Somerset, NJ (US); Donghui Wu, Bridgewater, NJ (US); Suman Chopra, Monroe, NJ (US); Andre M. Morgan, Robbinsville, NJ (US); Diane Cummins, Livingston, NJ (US); Lynette Zaidel, Cranford, NJ (US); Qin Wang, Monmouth Junction, NJ (US); Gary Edward Tambs, Belle Mead, NJ (US); Virginia Monsul Barnes, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 1498 days.

This patent is subject to a terminal disclaimer.

(21) Appl. No.: 12/058,360

(22) Filed: Mar. 28, 2008

(65) Prior Publication Data

US 2009/0202455 A1 Aug. 13, 2009

Related U.S. Application Data

(60) Provisional application No. 61/027,431, filed on Feb. 8, 2008, provisional application No. 61/027,420, filed on Feb. 8, 2008, provisional application No. 61/027,432, filed on Feb. 8, 2008.

(51) Int. Cl.

| A61K 8/00 | (2006.01) |
|---|---|
| A61Q 11/00 | (2006.01) |
| A61K 8/25 | (2006.01) |
| A61K 8/21 | (2006.01) |
| A61K 8/19 | (2006.01) |
| A61K 8/40 | (2006.01) |
| A61K 8/44 | (2006.01) |
| A61K 8/24 | (2006.01) |
| A61K 31/198 | (2006.01) |

(52) U.S. Cl.
CPC .............. *A61K 8/44* (2013.01); *A61K 8/19* (2013.01); *A61K 8/21* (2013.01); *A61K 8/24* (2013.01); *A61K 31/198* (2013.01); *A61Q 11/00* (2013.01)

(58) Field of Classification Search
USPC ..................... 424/52, 54, 682, 687
See application file for complete search history.

(56) References Cited

U.S. PATENT DOCUMENTS

| 3,535,421 A | 10/1970 | Briner et al. |
|---|---|---|
| 3,538,230 A | 11/1970 | Morton et al. |
| 3,678,154 A | 7/1972 | Widder et al. |
| 3,696,191 A | 10/1972 | Weeks |
| 3,862,307 A | 1/1975 | Di Giulio |
| 3,925,543 A | 12/1975 | Donohue |
| 3,932,605 A | 1/1976 | Vit |
| 3,932,608 A | 1/1976 | Anderson et al. |
| 3,937,807 A | 2/1976 | Haefele |
| 3,943,241 A | 3/1976 | Anderson et al. |
| 3,959,458 A | 5/1976 | Agricola et al. |
| 3,988,434 A | 10/1976 | Schole et al. |
| 3,991,177 A | 11/1976 | Vidra et al. |
| 4,011,309 A | 3/1977 | Lutz |
| 4,022,880 A | 5/1977 | Vinson et al. |
| 4,025,616 A | 5/1977 | Haefele |
| 4,042,680 A | 8/1977 | Muhler et al. |
| 4,051,234 A | 9/1977 | Gieske et al. |
| 4,058,595 A | 11/1977 | Colodney |
| 4,064,138 A | 12/1977 | Saari et al. |
| 4,100,269 A | 7/1978 | Pader |
| 4,108,979 A | 8/1978 | Muhler et al. |
| 4,108,981 A | 8/1978 | Muhler et al. |
| 4,110,083 A * | 8/1978 | Benedict .................. 51/295 |
| 4,146,607 A | 3/1979 | Ritchey |
| 4,154,813 A | 5/1979 | Kleinberg |
| 4,154,815 A | 5/1979 | Pader |
| 4,160,821 A | 7/1979 | Sipos |

(Continued)

FOREIGN PATENT DOCUMENTS

| EP | 0 569 666 A | 11/1993 |
|---|---|---|
| EP | 0579333 | 1/1994 |

(Continued)

OTHER PUBLICATIONS

US 5,989,525, 11/1999, Kleinberg et al. (withdrawn)
Machado et al., "CaviStat Confection Inhibition of Caries in Posterior Teeth," 83rd Session of the American Association for Dental Research, Mar. 21-24, 2007, Abstract, New Orleans Louisiana.
Chatterjee et al., "Bacterial Acidification and CaviStat Alkalinization of Occlusal Fissure pH," 83rd Session of the American Association for Dental Research, Mar. 9-12, 2005, Baltimore, MDal.
Kleinberg, I., "A Mixed-Bacteria Ecological Apporach to Understanding the Role of the Oral Bacteria in Dental Caries Causation: An Alternative to *Streptococcus mutans* and the Specific-Plaque Hypothesis," Crit. Rev. Oral Biol. Med., (2002) pp. 108-125 12:2.
Kleinberg, I., "A New Saliva-Based Anticaries Composition," Dentistry Today, Feb. 1999 18:2.

(Continued)

*Primary Examiner* — Lezah Roberts

(57) ABSTRACT

This invention relates to oral care compositions comprising an effective amount of a salt of a basic amino acid the salt having a pH in an unbuffered solution of less than about 7.5; an effective amount of a soluble fluoride salt; and a particulate material which has a pH in an unbuffered solution of less than about 7.5; and to methods of using and of making such compositions.

18 Claims, No Drawings

(56) References Cited

U.S. PATENT DOCUMENTS

| | | |
|---|---|---|
| 4,213,961 A | 7/1980 | Curtis et al. |
| 4,225,579 A | 9/1980 | Kleinberg |
| 4,259,316 A | 3/1981 | Nakashima et al. |
| 4,269,822 A | 5/1981 | Pellico et al. |
| 4,305,928 A | 12/1981 | Harvey |
| 4,335,102 A | 6/1982 | Nakashima et al. |
| 4,339,432 A | 7/1982 | Ritchey et al. |
| 4,340,583 A | 7/1982 | Wason |
| 4,355,022 A | 10/1982 | Rabussay |
| RE31,181 E | 3/1983 | Kleinberg |
| 4,466,954 A | 8/1984 | Ichikawa et al. |
| 4,528,181 A | 7/1985 | Morton et al. |
| 4,532,124 A | 7/1985 | Pearce |
| 4,538,990 A | 9/1985 | Pashley |
| 4,645,662 A | 2/1987 | Nakshima et al. |
| 4,656,031 A | 4/1987 | Lane et al. |
| 4,725,576 A | 2/1988 | Pollock et al. |
| 4,842,847 A | 6/1989 | Amjad |
| 4,866,161 A | 9/1989 | Sikes et al. |
| 4,885,155 A | 12/1989 | Parran, Jr. et al. |
| 4,992,420 A | 2/1991 | Neeser |
| 4,997,640 A | 3/1991 | Bird et al. |
| 5,000,939 A | 3/1991 | Dring et al. |
| 5,004,597 A | 4/1991 | Majeti et al. |
| 5,032,386 A * | 7/1991 | Gaffar et al. .................. 424/49 |
| 5,043,154 A * | 8/1991 | Gaffar et al. .................. 424/49 |
| 5,096,700 A | 3/1992 | Seibel et al. |
| 5,286,480 A | 2/1994 | Boggs et al. |
| 5,334,617 A | 8/1994 | Ulrich et al. |
| 5,370,865 A | 12/1994 | Yamagishi et al. |
| 5,427,755 A | 6/1995 | Dany et al. |
| 5,639,795 A | 6/1997 | Friedman et al. |
| 5,747,004 A | 5/1998 | Giani et al. |
| 5,762,911 A | 6/1998 | Kleinberg et al. |
| 5,906,811 A | 5/1999 | Hersh |
| 5,922,346 A | 7/1999 | Hersh |
| 5,997,301 A | 12/1999 | Linden |
| 6,217,851 B1 | 4/2001 | Kleinberg et al. |
| 6,436,370 B1 | 8/2002 | Kleinberg et al. |
| 6,488,961 B1 | 12/2002 | Robinson et al. |
| 6,524,558 B2 | 2/2003 | Kleinberg et al. |
| 6,558,654 B2 | 5/2003 | McLaughlin |
| 6,805,883 B2 | 10/2004 | Chevaux et al. |
| 8,281,597 B2 | 10/2012 | Li et al. |
| 2002/0064504 A1* | 5/2002 | Kleinberg et al. ............. 424/49 |
| 2002/0081360 A1 | 6/2002 | Burgard et al. |
| 2003/0133885 A1 | 7/2003 | Kleinberg et al. |
| 2004/0185027 A1 | 9/2004 | Reierson et al. |
| 2007/0154863 A1 | 7/2007 | Cai et al. |
| 2010/0330003 A1 | 12/2010 | Robinson et al. |

FOREIGN PATENT DOCUMENTS

| | | |
|---|---|---|
| JP | H4-128216 | 4/1992 |
| JP | H6-192060 | 7/1994 |
| JP | H07-258053 | 10/1995 |
| JP | H8-151324 | 6/1996 |
| JP | H10-245328 | 9/1998 |
| JP | H11-246374 | 9/1999 |
| JP | 2004-244404 | 9/2004 |
| JP | 2005-008579 | 1/2005 |
| RU | 2132182 | 6/1999 |
| RU | 2287318 | 11/2005 |
| WO | 9732565 A | 9/1997 |
| WO | 2007011552 A | 1/2007 |
| WO | 2007068916 A | 6/2007 |
| WO | WO 2009/099450 | 8/2009 |
| WO | WO 2009/099451 | 8/2009 |
| WO | WO 2009/099452 | 8/2009 |
| WO | WO 2009/099454 | 8/2009 |
| WO | WO 2009/099455 | 8/2009 |

OTHER PUBLICATIONS

Packaging with ingredient list for DenClude (launched Dec. 2004).
Packaging with ingredient list for ProClude (launched Jul. 2002).
International Search Report PCT/US2008/058696 Dated Jan. 5, 2009.
Garfar, A. et al., "Antiplaque effects of dentifrices containing triclosan/copolymer/NaF system versus triclosan dentifrices without the copolymer," American Journal of Dentistry, Sep. 1990, 3:S7-S14.

* cited by examiner

ORAL CARE PRODUCT AND METHODS OF USE AND MANUFACTURE THEREOF

This application claims the benefit of U.S. Ser. No. 61/027,420 filed Feb. 8, 2008, U.S. Ser. No. 61/027,431 filed Feb. 8, 2008, and U.S. Ser. No. 61/027,432 filed Feb. 8, 2008 the contents of which are incorporated herein by reference.

FIELD OF THE INVENTION

This invention relates to oral care compositions, for example comprising a salt of a basic amino acid having a pH in solution of less than 7.5, an abrasive having a pH in solution of less than 7.5, and a fluoride ion source, and to methods of using and of making these compositions.

BACKGROUND OF THE INVENTION

Arginine and other basic amino acids have been proposed for use in oral care and are believed to have significant benefits in combating cavity formation and tooth sensitivity. Combining these basic amino acids with minerals having oral care benefits, e.g., fluoride and calcium, to form an oral care product having acceptable long term stability, however, has proven challenging. In particular, the basic amino acid may raise the pH and facilitate dissociation of calcium ions that can react with fluoride ions to form an insoluble precipitate. Moreover, the higher pH has the potential to cause irritation. At neutral pH or acidic pH, however, a system utilizing arginine bicarbonate (which the art teaches is preferred) may release carbon dioxide, leading to bloating and bursting of the containers. Moreover, it might be expected that lowering the pH to neutral or acidic conditions would reduce the efficacy of the formulation because the arginine may form an insoluble arginine-calcium complex that has a poorer affinity for the tooth surface, and moreover that lowering the pH would reduce any effect the formulation might have on buffering cariogenic lactic acid in the mouth. Partly because of these unaddressed formulation hurdles and partly because arginine has generally been viewed in the art as a potential alternative to fluoride rather than a co-active, there has been little motivation to make oral care products comprising both arginine and fluoride. Additional hurdles are potentially posed by addition of an antimicrobial agent. Commercially available arginine-based toothpaste, such as ProClude® and DenClude®, for example, contain arginine bicarbonate and calcium carbonate, but not fluoride nor any antimicrobial agent.

Accordingly, there is a need for a stable oral care product that provides a basic amino acid and also provides beneficial minerals such as fluoride and calcium.

BRIEF SUMMARY OF THE INVENTION

The invention encompasses oral care compositions and methods of using the same that are effective in inhibiting or reducing the accumulation of plaque, reducing levels of acid producing (cariogenic) bacteria, remineralizing teeth, and inhibiting or reducing gingivitis. The invention also encompasses compositions and methods to clean the oral cavity and provide improved methods of promoting oral health and/or systemic health, including cardiovascular health, e.g., by reducing potential for systemic infection via the oral tissues.

The invention thus comprises an oral care composition (a Composition of the Invention), e.g., a dentifrice, comprising
i. an effective amount of a salt of a basic amino acid, e.g., arginine, e.g., present in an amount of at least about 1%, for example about 1 to about 15%, having a pH in an unbuffered solution of less than about 7.5, e.g., about 6 to about 7.4, e.g., about 6.8 to about 7.2, e.g., approximately neutral pH;
ii. an effective amount of a soluble fluoride salt, e.g., sodium fluoride, stannous fluoride or sodium monofluorophosphate, e.g., providing from about 100 to 25,000 ppm, e.g., about 750 to about 2000 ppm fluoride ions;
iii. a particulate material, e.g., silica or dicalcium phosphate, which has a pH in an unbuffered solution of less than about 7.5, e.g., about 6.5 to about 7.4, e.g., about 6.8 to about 7.2, e.g., approximately neutral pH.

In one embodiment the invention encompasses a Composition of the Invention (Composition 1.1) comprising
i. an effective amount of a salt of (a) an inorganic acid, e.g., an inorganic oxoacid, and (b) a basic amino acid;
ii. a salt of an inorganic acid, e.g., an inorganic oxoacid, and calcium; and
iii. an effective amount of a soluble fluoride salt.
The inorganic acid may be an inorganic oxoacid, for example phosphoric acid. The basic amino acid may be for example arginine. The fluoride salt may be for example sodium monofluorophosphate. Thus, Compositions of the Invention thus include a dentifrice comprising (i) arginine phosphate, (ii) dicalcium phosphate dihydrate, and (iii) sodium monofluorophosphate.

In another embodiment, the invention encompasses a Composition of the Invention (Composition 1.2) comprising
i. an effective amount of a salt of a basic amino acid;
ii. an effective amount of a soluble fluoride salt;
iii. an anionic surfactant. e.g., sodium lauryl sulfate.

In another embodiment, the invention encompasses a Composition of the Invention (Composition 1.3) comprising
i. an effective amount of a salt of a basic amino acid;
ii. an effective amount of a soluble fluoride salt;
iii. an antibacterial agent, e.g., triclosan;
iv. optionally, an anionic surfactant, e.g., sodium lauryl sulfate;
v. optionally, an anionic polymer. e.g., a copolymer of methyl vinyl ether and maleic anhydride.

In another embodiment, the invention encompasses a Composition of the Invention (Composition 1.4) comprising
i. an effective amount of a salt of a basic amino acid:
ii. an effective amount of a soluble fluoride salt; and
iii. small particle abrasive having a RDA of about less than 160, e.g., about 40 to about 140, e.g., comprising at least about 5% of an abrasive having a d50 less than about 5 micrometers, e.g., silica having a d50 of about 3 to about 4 micrometers.

In particular embodiments, the Compositions of the Invention are in the form of a dentifrice comprising additional ingredients selected from one or more of water, abrasives, surfactants, foaming agents, vitamins, polymers, enzymes, humectants, thickeners, antimicrobial agents, preservatives, flavorings, colorings and/or combinations thereof.

Without intending to be bound by a particular theory, it is hypothesized that a significant factor in the beneficial effect of arginine is that arginine and other basic amino acids can be metabolized by certain types of bacteria, e.g., *S. sanguis* which are not cariogenic and which compete with cariogenic bacteria such as *S. mutans*, for position on the teeth and in the oral cavity. The arginolytic bacteria can use arginine and other basic amino acids to produce ammonia, thereby raising the pH of their environment, while cariogenic bacteria metabolize sugar to produce lactic acid, which tends to lower the plaque pH and demineralize the teeth, ultimately leading to cavities. It is believed that regular use of a Composition of the Invention, over time, will lead to a relative increase in the arginolytic bacteria and a relative decrease in the cariogenic bacteria, resulting in a higher plaque pH (notwithstanding that the Composition of the Invention is itself generally pH neutral, the basic amino acid having been neutralized by an inorganic oxoacid). It is believed that this pH-raising effect may be mechanistically separate from and complementary to the effect of fluoride in promoting remineralization and strengthening the tooth enamel.

Irrespective of the precise mechanism, however, it is surprisingly found that the combination of fluoride and a basic amino acid. e.g., arginine, in an oral care product according to the present invention produces unexpected benefits beyond and qualitatively different from what can be observed using compositions comprising effective amounts of either compound separately, in promoting remineralization, repairing early enamel lesions, and enhancing oral health. It has moreover been found that this action can be further enhanced by addition of a small particle abrasive, which may act to help fill microfissures in the enamel and microtubules in the dentin.

The presence of a basic amino acid is also surprisingly found to reduce bacterial adhesion to the tooth surface, particularly when the basic amino acid is provided in combination with an anionic surfactant. The combination of the basic amino acid and the anionic surfactant also enhances delivery of antimicrobial agents, particularly triclosan.

The invention thus further encompasses methods to (i) reduce or inhibit formation of dental caries, (ii) reduce, repair or inhibit early enamel lesions, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat dry mouth, and/or (xiii) clean the teeth and oral cavity, comprising applying a Composition of the Invention to the oral cavity, e.g., by applying a Composition of the Invention to the oral cavity of a patient in need thereof.

DETAILED DESCRIPTION OF THE INVENTION

General Description

The invention thus comprises an oral care composition (Composition 1.0) comprising
i. an effective amount of a salt of a basic amino acid, e.g., arginine, e.g., present in an amount of at least about 1%, for example about 1 to about 15%, having a pH in an unbuffered solution of less than about 7.5, e.g., about 6.5 to about 7.4, e.g., about 6.8 to about 7.2, e.g., approximately neutral pH;
ii. an effective amount of a fluoride source, e.g., a soluble fluoride salt, e.g., sodium monofluorophosphate, providing from about 100 to 25,000 ppm fluoride ions, e.g., about 750 to about 2000 ppm;
iii. a particulate, e.g., silica or dicalcium phosphate, which has a pH in an unbuffered solution of less than about 7.5, e.g., about 6 to about 7.4, e.g., about 6.8 to about 7.2, e.g., approximately neutral pH;
for example any of the following compositions:
1.0.1. Composition 1.0 wherein the basic amino acid is arginine, lysine, citrullene, ornithine, creatine, histidine, diaminobutanoic acid, diaminoproprionic acid, salts thereof and/or combinations thereof.
1.0.2. Composition 1.0 or 1.0.1 wherein the basic amino acid has the L-configuration.
1.0.3. Any of the preceding compositions is provided in the form of a salt of a di- or tri-peptide comprising the basic amino acid.
1.0.4. Any of the preceding compositions wherein the basic amino acid is arginine.
1.0.5. Any of the preceding compositions wherein the basic amino acid is L-arginine.
1.0.6. Any of the preceding compositions wherein the salt of the basic amino acid is arginine phosphate.
1.0.7. Any of the preceding compositions wherein the salt of the basic amino acid is arginine hydrochloride.
1.0.8. Any of the preceding compositions wherein the salt of the basic amino acid is arginine sulfate.
1.0.9. Any of the preceding compositions wherein the salt of the basic amino acid is formed in situ in the formulation by neutralization of the basic amino acid with an acid or a salt of an acid.
1.0.10. Any of the preceding compositions wherein the salt of the basic amino acid is formed by neutralization of the basic amino acid to form a premix prior to combination with the fluoride salt.
1.0.11. Any of the preceding compositions wherein the basic amino acid is present in an amount corresponding to about 0.1 to about 20%, e.g., about 1 wt. % to about 15 wt. %, of the total composition weight, the weight of the basic amino acid being calculated as free base form.
1.0.12. Composition 1.0.11 wherein the basic amino acid is present in an amount of about 7.5 wt. % of the total composition weight.
1.0.13. Composition 1.0.11 wherein the basic amino acid is present in an amount of about 5 wt. % of the total composition weight.
1.0.14. Composition 1.0.11 wherein the basic amino acid is present in an amount of about 3.75 wt. % of the total composition weight.
1.0.15. Composition 1.0.11 wherein the basic amino acid is present in an amount of about 1.5 wt. % of the total composition weight.
1.0.16. Any of the preceding compositions wherein the fluoride salt is stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate and combinations thereof.
1.0.17. Any of the preceding compositions wherein the fluoride salt is a fluorophosphate.
1.0.18. Any of the preceding composition wherein the fluoride salt is sodium monofluorophosphate.
1.0.19. Any of the preceding compositions wherein the fluoride salt is present in an amount of about 0.01 wt. % to about 2 wt. % of the total composition weight.
1.0.20. Any of the preceding compositions wherein the soluble fluoride salt provides fluoride ion in an amount of about 0.1 to about 0.2 wt. % of the total composition weight.
1.0.21. Any of the preceding compositions wherein the soluble fluoride salt provides fluoride ion in an amount of from about 50 to 25,000 ppm.
1.0.22. Any of the preceding compositions which is a mouthwash having about 100 to about 250 ppm available fluoride ion.

1.0.23. Any of which is a dentifrice having about 750 to about 2000 ppm available fluoride ion.
1.0.24. Any of the preceding compositions wherein the composition comprises about 750 to about 2000 ppm fluoride ion.
1.0.25. Any of the preceding compositions wherein the composition comprises about 1000 to about 1500 ppm fluoride ion.
1.0.26. Any of the preceding compositions wherein the composition comprises about 1450 ppm fluoride ion.
1.0.27. Any of the preceding compositions wherein the pH is between about 6 and about 7.4.
1.0.28. Any of the preceding compositions wherein the pH is between about 6.8 and about 7.2.
1.0.29. Any of the preceding compositions wherein the pH is approximately neutral.
1.0.30. Any of the preceding compositions further comprising an abrasive or particulate material.
1.0.31. The immediately preceding composition wherein the abrasive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof.
1.0.32. The immediately preceding composition wherein the abrasive or particulate is selected from a calcium phosphate (e.g., dicalcium phosphate dihydrate), calcium sulfate, precipitated calcium carbonate, silica (e.g., hydrated silica), and combinations thereof.
1.0.33. Any of the preceding compositions comprising an abrasive in an amount of about 15 wt. % to about 70 wt. % of the total composition weight.
1.0.34. Any of the preceding compositions comprising a small particle abrasive fraction of at least about 5% having a d50 of less than about 5 micrometers.
1.0.35. Any of the preceding compositions having a RDA of less than about 150, e.g., about 40 to about 140.
1.0.36. Any of the preceding compositions comprising at least one surfactant.
1.0.37. Any of the preceding compositions comprising at least one surfactant selected from sodium lauryl sulfate, cocamidopropyl betaine, and combinations thereof.
1.0.38. Any of the preceding compositions comprising an anionic surfactant.
1.0.39. Any of the preceding compositions comprising sodium lauryl sulfate.
1.0.40. Any of the preceding compositions comprising at least one humectant.
1.0.41. Any of the preceding compositions comprising at least one humectant selected from glycerin, sorbitol and combinations thereof.
1.0.42. Any of the preceding compositions comprising at least one polymer.
1.0.43. Any of the preceding compositions comprising at least one polymer selected from polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum), and combinations thereof.
1.0.44. Any of the preceding compositions comprising gum strips or fragments.
1.0.45. Any of the preceding compositions comprising flavoring, fragrance and/or coloring.
1.0.46. Any of the preceding compositions comprising water.
1.0.47. Any of the preceding compositions comprising an antibacterial agent.
1.0.48. Any of the preceding compositions comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, seabuckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing.
1.0.49. Any of the preceding compositions comprising an anti-inflammatory compound. e.g., an inhibitor of at least one of host pro-inflammatory factors selected from matrix metalloproteinases (MMP's), cyclooxygenases (COX), $PGE_2$, interleukin 1 (IL-1). IL-1β converting enzyme (ICE), transforming growth factor β1 (TGF-β1), inducible nitric oxide synthase (iNOS), hyaluronidase, cathepsins, nuclear factor kappa B (NF-κB), and IL-1 Receptor Associated Kinase (IRAK), e,g, selected from aspirin, ketorolac, flurbiprofen, ibuprofen, naproxen, indomethacin, aspirin, ketoprofen, piroxicam, meclofenamic acid, nordihydoguaiaretic acid, and mixtures thereof.
1.0.50. Any of the preceding compositions comprising a whitening agent.
1.0.51. Any of the preceding compositions comprising a whitening agent selected from a whitening active selected from the group consisting of peroxides, metal chlorites, perborates, percarbonates, peroxyacids, hypochlorites, and combinations thereof.
1.0.52. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate), or hydrogen peroxide polymer complexes such as hydrogen peroxide-polyvinyl pyrrolidone polymer complexes.
1.0.53. Any of the preceding compositions comprising an antioxidant, e.g., selected from the group consisting of Co-enzyme Q10, PQQ, Vitamin D, Vitamin C, Vitamin E, Vitamin A, anethole-dithiothione, and mixtures thereof.
1.0.54. Any of the preceding compositions comprising triclosan.
1.0.55. Any of the preceding composition comprising triclosan and $Zn^{2+}$ ion source, e.g., zinc citrate.
1.0.56. Any of the preceding compositions comprising an antibacterial agent in an amount of about 0.01 to about 5 wt. % of the total composition weight.

1.0.57. Any of the preceding compositions comprising triclosan in an amount of about 0.01 to about 1 wt. percent of the total composition weight.
1.0.58. Any of the preceding compositions comprising triclosan in an amount of about 0.3% of the total composition weight.
1.0.59. Any of the preceding compositions further comprising an agent that interferes with or prevents bacterial attachment, e.g., solbrol or chitosan.
1.0.60. Any of the preceding compositions further comprising an anti-calculus agent.
1.0.61. Any of the preceding compositions further comprising an anti-calculus agent which is a polyphosphate, e.g., pyrophosphate, tripolyphosphate, or hexametaphosphate, e.g., in sodium salt form.
1.0.62. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate.
1.0.63. Any of the preceding compositions further comprising a soluble calcium salt, e.g., selected from calcium sulfate, calcium chloride, calcium nitrate, calcium acetate, calcium lactate, and combinations thereof.
1.0.64. Any of the preceding compositions further comprising a physiologically acceptable potassium salt, e.g., potassium nitrate or potassium chloride, in an amount effective to reduce dentinal sensitivity.
1.0.65. Any of the preceding compositions comprising from about 0.1% to about 7.5% of a physiologically acceptable potassium salt, e.g., potassium nitrate and/or potassium chloride.
1.0.66. Any of the preceding compositions effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) treat, relieve or reduce dry mouth, (xiii) clean the teeth and oral cavity, (xiv) reduce erosion, (xv) whiten teeth, (xvi) immunize the teeth against cariogenic bacteria and/or (xvii) promote systemic health, including cardiovascular health, e.g., by reducing potential for systemic infection via the oral tissues.
1.0.67. A composition obtained or obtainable by combining the ingredients as set forth in any of the preceding compositions.
1.0.68. Any of the preceding compositions in a form selected from mouthrinse, toothpaste, tooth gel, tooth powder, non-abrasive gel, mousse, foam, mouth spray, lozenge, oral tablet, dental implement, and pet care product.
1.0.69. Any of the preceding compositions wherein the composition is toothpaste.
1.0.70. Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.
1.0.71. Any of the preceding compositions 1.0-1.0.67 wherein the composition is a mouthwash.

In one embodiment the invention encompasses an oral care composition (Composition 1.1), e.g., according to any of the preceding Compositions 1.0-1.0.71, comprising
i. a salt of an inorganic acid and a basic amino acid,
ii. a calcium salt: and
iii. a soluble fluoride salt.

The invention thus comprises, e.g., the following embodiments of Composition 1.1:
1.1.1. Composition 1.1 wherein the inorganic acid which forms a salt with a basic amino acid is an inorganic oxoacid.
1.1.2. Composition 1.1.1 wherein the inorganic oxoacid is selected from phosphoric acid and sulfuric acid.
1.1.3. Composition 1.1.2 wherein the salt of an inorganic oxoacid and a basic amino acid is the phosphate salt.
1.1.4. Any of the foregoing compositions wherein the calcium salt is a salt of calcium and an inorganic acid.
1.1.5. Composition 1.1.4 wherein the calcium salt is a salt of calcium and an inorganic oxoacid, e.g., calcium phosphate or calcium sulfate or mixtures thereof.
1.1.6. Composition 1.1.5 wherein the calcium salt is a calcium phosphate.
1.1.7. Composition 1.1.6 wherein the calcium salt is dicalcium phosphate ($CaHPO_4$).
1.1.8. Composition 1.1.7 wherein the dicalcium phosphate is in the form of the dihydrate ($CaHPO_4.2H_2O$).
1.1.9. Compositions 1.5 et seq. wherein the calcium salt is calcium sulfate ($CaSO_4$).
1.1.10. Any of the foregoing Compositions 1.1 et seq. wherein the anion of (i) the salt of the basic amino acid and (ii) the calcium salt, is the same.
1.1.11. Any of the foregoing Compositions 1.1 et seq. comprising at least one phosphate salt of a basic amino acid; (ii) at least one calcium phosphate salt; and (iii) at least one soluble fluoride salt.
1.1.12. Any of the foregoing Compositions 1.1 et seq. wherein the basic amino acid is arginine, lysine, citrullene, ornithine, creatine, histidine, diaminobutanoic acid, diaminoproprionic acid, salts thereof or combinations thereof.
1.1.13. Any of the foregoing Compositions 1.1 et seq. wherein the basic amino acid has the L-configuration.
1.1.14. Any of the foregoing Compositions 1.1 et seq. wherein the salt of the inorganic oxoacid and the basic amino acid is formed by reaction of the basic amino acid with the inorganic oxoacid and/or (ii) alkali or ammonium salts thereof.
1.1.15. Any of the foregoing Compositions 1.1 et seq. comprising a phosphate salt of a basic amino acid formed by reaction of the basic amino acid with phosphoric acid or with an alkali or ammonium salt of phosphoric acid.
1.1.16. Any of the foregoing Compositions 1.1 et seq. wherein the basic amino acid is arginine or a salt thereof.
1.1.17. Any of the foregoing Compositions 1.1 et seq. comprising arginine phosphate.
1.1.18. Any of the foregoing Compositions 1.1 et seq. wherein the fluoride salt is stannous fluoride, sodium fluoride, potassium fluoride, sodium monofluorophosphate, sodium fluorosilicate, ammonium fluorosilicate, amine fluoride, ammonium fluoride, and combinations thereof.
1.1.19. Any of the foregoing Compositions 1.1 et seq. wherein the fluoride source is a fluorophosphate.
1.1.20. Any of the preceding composition wherein the fluoride source is sodium monofluorophosphate.

1.1.21. Any of the foregoing Compositions 1.1 et seq. wherein the basic amino acid is present in an amount corresponding to about 1 wt. % to about 10 wt. % of the total composition weight, the weight of the basic amino acid being calculated as free base form.

1.1.22. Composition 1.1.18 wherein the basic amino acid is present in an amount of about 7.5 wt. % of the total composition weight.

1.1.23. Composition 1.1.18 wherein the basic amino acid is present in an amount of about 5 wt. % of the total composition weight.

1.1.24. Composition 1.1.18 wherein the basic amino acid is present in an amount of about 3.75 wt. % of the total composition weight.

1.1.25. Composition 1.1.18 wherein the basic amino acid is present in an amount of about 1.5 wt. % of the total composition weight.

1.1.26. Any of the foregoing Compositions 1.1 et seq. wherein the calcium salt is present in an amount of about 20 wt. % to about 60 wt. % of the total composition weight.

1.1.27. Any of the foregoing Compositions 1.1 et seq. wherein calcium phosphate is present in an amount of about 40 wt. % to about 50 wt. % of the total composition weight.

1.1.28. Any of the foregoing Compositions 1.1 et seq. wherein a phosphate of the basic amino acid is formed by reaction with phosphoric acid or phosphate salts to provide an approximately neutral pH, e.g., about pH 6.8 to about pH 7.2.

1.1.29. Any of the foregoing Compositions 1.1 et seq. wherein a sulfate of the basic amino acid is formed by reaction with sulfuric acid or sulfate salts to provide an approximately neutral pH, e.g., about pH 6.8 to about pH 7.2.

1.1.30. Any of the foregoing Compositions 1.1 et seq. wherein the fluoride salt is present in an amount of about 0.01 wt. % to about 2 wt. % of the total composition weight.

1.1.31. Any of the foregoing Compositions 1.1 et seq. wherein the fluoride salt provides fluoride ion in an amount of about 0.1 to about 0.2 wt. % of the total composition weight.

1.1.32. Any of the foregoing Compositions 1.1 et seq., e.g., in the form of a dentifrice. wherein the composition comprises about 500 to about 15,000 ppm fluoride ion.

1.1.33. Any of the foregoing Compositions 1.1 et seq. wherein the composition comprises about 1000 to about 1500 ppm fluoride ion.

1.1.34. Any of the foregoing Compositions 1.1 et seq. wherein the composition comprises about 1450 ppm fluoride ion.

1.1.35. Any of the foregoing Compositions 1.1 et seq. wherein the pH is less than about 7.5.

1.1.36. Any of the preceding compositions wherein the pH is between about 6 and about 7.3.

1.1.37. Any of the foregoing Compositions 1.1 et seq. wherein the pH is between about 6.8 and about 7.2.

1.1.38. Any of the foregoing Compositions 1.1 et seq. effective upon application to the oral cavity, e.g., with brushing, to (i) reduce or inhibit formation of dental caries, (ii) reduce, repair or inhibit pre-carious lesions of the enamel, e.g., as detected by quantitative light-induced fluorescence (QLF) or electrical caries measurement (ECM), (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of arginolytic bacteria, (ix) inhibit microbial biofilm formation in the oral cavity, (x) raise and/or maintain plaque pH at levels of at least pH 5.5 following sugar challenge, (xi) reduce plaque accumulation, (xii) reduce dry mouth, (xiii) clean the teeth and oral cavity (xiv) reduce erosion, (xv) whiten teeth, and/or (xvi) immunize the teeth against cariogenic bacteria.

1.1.39. Any of the foregoing Compositions 1.1 et seq. comprising the phosphate of a basic amino acid, a phosphate abrasive material, and a fluorophosphate.

1.1.40. Any of the foregoing Compositions 1.1 et seq. comprising arginine phosphate, dicalcium phosphate dihydrate, and sodium monofluorophosphate.

1.1.41. Any of the foregoing Compositions 1.1 et seq. obtained or obtainable by the steps of combining a basic amino acid with phosphoric acid, an inorganic phosphate salt, or a combination thereof to obtain a pH of about 7 to form a premix, which is used to make the desired composition.

1.1.42. Any of the foregoing Compositions 1.1 et seq. obtained or obtainable by the steps of combining a basic amino acid with phosphoric acid, an inorganic phosphate salt, or a combination thereof to obtain a pH of about 7 to form a premix, and combining the premix with dicalcium phosphate, and a fluoride ion source.

1.1.43. Any of the foregoing Compositions 1.1 et seq. obtained or obtainable by any of Method 2, et seq. as hereinafter set forth.

1.1.44. A composition obtained or obtainable by combining the ingredients as set forth in any of the preceding compositions.

1.1.45. Any of the foregoing Compositions 1.1 et seq. wherein the composition is toothpaste.

1.1.46. Composition 1.1.42 wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.1.47. Any of the foregoing Compositions 1.1-1.1.41 wherein the composition is a mouthwash.

In another embodiment, the invention encompasses a Composition of the Invention (Composition 1.2), e.g., according to any of the preceding Compositions 1.0-1.0.71, comprising
i. an effective amount of a salt of a basic amino acid;
ii. an effective amount of a soluble fluoride salt:
iii. an anionic surfactant, e.g., sodium lauryl sulfate.

In another embodiment, the invention encompasses a Composition of the Invention (Composition 1.3) e.g., according to any of the preceding Compositions 1.0-1.0.71, comprising
i. an effective amount of a salt of a basic amino acid;
ii. an effective amount of a soluble fluoride salt;
iii. an anionic surfactant, e.g., sodium laurel sulfate;
iv. an anionic polymer, e.g., a copolymer of methyl vinyl ether and maleic anhydride; and
v. an antibacterial agent, e.g., triclosan.

In another embodiment, the invention encompasses a Composition of the Invention (Composition 1.4) e.g., according to any of the preceding Compositions 1.0-1.0.71, comprising
i. an effective amount of a salt of a basic amino acid;
ii. an effective amount of a soluble fluoride salt; and
iii. a particulate material, the composition having an RDA of less than about 160, e.g., about 40 to about 140, e.g., comprising at least about 5% of a particulate having a d50 less than about 5 micrometers, e.g., silica having a d50 of about 3 to about 4 micrometers.

In another embodiment, the invention encompasses a method (Method 2) for preparing an oral composition, e.g., any Compositions under 1.0, 1.1, 1.2, 1.3 or 1.4 supra, comprising i. forming a premix by combining a basic amino acid in a gel phase with an acid and/or salt thereof to obtain a pH of less than about 7.5, and
ii. combining the premix with other ingredients of the formulation, including a soluble fluoride salt.

Method 2 thus comprises, e.g., the following embodiments:

2.1. Method 2 wherein the acid combined with the basic amino acid is a mineral acid.
2.2. Method 2.1 wherein the mineral acid is an inorganic oxoacid.
2.3. Method 2.2 wherein the inorganic oxoacid is phosphoric acid.
2.4. Any of the preceding methods wherein the other ingredients of the formulation comprise a calcium phosphate salt.
2.5. The preceding method wherein the calcium phosphate is dicalcium phosphate dihydrate.
2.6. Any of the preceding methods wherein the fluoride salt is selected from stannous fluoride, sodium fluoride, potassium fluoride, sodium monofluorophosphate, sodium fluorosilicate, ammonium fluorosilicate, amine fluoride, ammonium fluoride, and combinations thereof.
2.7. Any of the preceding methods wherein the fluoride salt is a fluorophosphate.
2.8. Any of the preceding methods wherein the fluoride salt is sodium monofluorophosphate.
2.9. Any of the preceding methods wherein the basic amino acid is selected from arginine, lysine, citrullene, ornithine, creatine, histidine, diaminobutanoic acid, diaminopropionic acid, salts and combinations thereof.
2.10. Any of the preceding methods wherein the basic amino acid has the L-configuration.
2.11. Any of the preceding methods wherein the basic amino acid is arginine.
2.12. Any of the preceding methods wherein the premix has a pH of about 6 to about 7.3.
2.13. Any of the preceding methods wherein the premix has a pH of about 6.8 to about 7.2.
2.14. Any of the preceding methods wherein the premix has a pH of about 7.
2.15. Any of the preceding methods when carried out at room temperature and pressure.
2.16. Any of the preceding methods wherein the ingredients and their respective amounts are as set forth in any of the embodiments as set forth under Compositions 1.0, 1.1, 1.2, 1.3 or 1.4.

In another embodiment, the invention encompasses a method ((Method 3) to improve oral health comprising applying an effective amount of the oral composition of any of the embodiments under Compositions 1.0, 1.1, 1.2, 1.3 or 1.4, to the oral cavity of a subject in need thereof, e.g., a method to i. reduce or inhibit formation of dental caries,
ii. reduce, repair or inhibit early enamel lesions, e.g., as detected by quantitative light-induced fluorescence (QLF) or electrical caries measurement (ECM),
iii. reduce or inhibit demineralization and promote remineralization of the teeth,
iv. reduce hypersensitivity of the teeth,
v. reduce or inhibit gingivitis,
vi. promote healing of sores or cuts in the mouth,
vii. reduce levels of acid producing bacteria,
viii. to increase relative levels of arginolytic bacteria,
ix. inhibit microbial biofilm formation in the oral cavity,
x. raise and/or maintain plaque pH at levels of at least pH 5.5 following sugar challenge,
xi. reduce plaque accumulation,
xii. treat, relieve or reduce dry mouth,
xiii. clean the teeth and oral cavity,
xiv. reduce erosion,
xv. whiten teeth,
xvi. immunize the teeth against cariogenic bacteria; and/or
xvii. promote systemic health, including cardiovascular health, e.g., by reducing potential for systemic infection via the oral tissues.

The invention further comprises the use of arginine in the manufacture of a Composition of the Invention, e.g., for use in any of the indications set forth in Method 3.

The invention further provides an oral care composition comprising a basic amino acid, in free or salt form, a soluble fluoride salt and a calcium salt of an inorganic acid for use in the treatment of at least one of demineralized teeth and enamel lesions within an oral cavity of a subject, or for enhancing the mineralization of teeth within an oral cavity of a subject. It has been found surprisingly that such a composition exhibits enhanced treatment of teeth demineralization or lesions even before dental caries have been formed.

The invention further provides the use of a basic amino acid, in free or salt form, in an oral care composition comprising a soluble fluoride salt and a calcium salt of an inorganic acid for enhancing the mineralization of teeth within an oral cavity of a subject, and the use of a basic amino acid, in free or salt form, for the manufacture of a medicament which includes a soluble fluoride salt and a calcium salt of an inorganic acid for enhancing the mineralization of teeth within an oral cavity of a subject.

The invention further provides a method of mineralizing at least one of demineralized teeth and enamel lesions within an oral cavity of a subject, the method comprising treating the oral cavity with an oral care composition comprising a basic amino acid, in free or salt form, a soluble fluoride salt and a calcium salt of an inorganic acid.

The invention further provides an oral care composition comprising a salt of a basic amino acid neutralized by an inorganic acid for reducing or inhibiting the formation of dental caries by increasing the pH of plaque in an oral cavity of a subject when treated with the oral composition. It has been found surprisingly that such a composition exhibits increased plaque pH which can reduce or inhibit the formation of dental caries before dental caries have been formed.

The invention further provides the use of a salt of a basic amino acid neutralized by an inorganic acid in an oral care composition for reducing or inhibiting the formation of dental caries by increasing the pH of plaque in an oral cavity of a subject when treated with the oral composition, and the use of a salt of a basic amino acid neutralized by an inorganic acid for the manufacture of a medicament for use in reducing or inhibiting the formation of dental caries by increasing the pH of plaque in an oral cavity of a subject treated with the medicament.

The invention further provides a method of increasing the pH of plaque in an oral cavity of a subject, the method comprising treating the oral cavity with an oral care composition comprising a salt of a basic amino acid neutralized by an inorganic acid.

The invention further provides an oral care composition comprising a salt of a basic amino acid and an inorganic acid, a soluble fluoride salt and a calcium salt of an inorganic acid. It has been found surprisingly that such a composition exhibits enhanced fluoride stability in the composition over a period of time.

The invention further provides an oral care composition comprising a soluble fluoride salt and a calcium salt of an inorganic acid, and, in addition, a salt of a basic amino acid and an inorganic acid for increasing the stability of the fluoride in the composition.

The invention further provides a method of producing an oral care composition, the method comprising the steps of:
i. providing a basic amino acid and an inorganic acid, and neutralizing the basic amino acid with the inorganic acid to form a salt of the basic amino acid;
ii. combining the salt of the basic amino acid with at least a soluble fluoride salt and a calcium salt of an inorganic acid to form the oral care composition.

The invention further provides a method of producing an oral care composition, the method comprising the step of: combining together a basic amino acid component, a soluble fluoride salt and a calcium salt of an inorganic acid, wherein for increasing the stability of the fluoride in the composition, the basic amino acid is neutralized with an inorganic acid to form a salt of the basic amino acid prior to the combining step.

The invention further provides the use, in an oral care composition, of a salt of a basic amino acid, the salt being formed by neutralizing the basic amino acid with an inorganic acid, as an additive for an oral care composition, comprising at least a soluble fluoride salt and a calcium salt of an inorganic acid, for increasing the stability of the fluoride in the composition.

It may therefore be seen by the skilled practitioner in the oral care art that a number of different yet surprising technical effects and advantages can result from the formulation, and use, of an oral care composition, for example a dentifrice, in accordance with one or more aspects of the invention, which are directed to the provision of different combinations of active components or ingredients, and preferably their respective amounts, within the composition.

Levels of active ingredients will vary based on the nature of the delivery system and the particular active. For example, the basic amino acid may be present at levels from, e.g., about 0.1 to about 20 wt % (expressed as weight of free base), e.g., about 0.1 to about 3 wt % for a mouthrinse about 1 to about 10 wt % for a consumer toothpaste or about 7 to about 20 wt % for a professional or prescription treatment product. Fluoride may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial will vary similarly, with levels used in toothpaste being e.g., about 5 to about 15 times greater than used in mouthrinse. For example, a triclosan mouthrinse may contain. e.g., about 0.03 wt % triclosan while a triclosan toothpaste may contain about 0.3 wt % triclosan.

Basic Amino Acids

The basic amino acids which can be used in the compositions and methods of the invention include not only naturally occurring basic amino acids, such as arginine, lysine, and histidine, but also any basic amino acids having a carboxyl group and an amino group in the molecule, which are water-soluble and provide an aqueous solution with a pH of 7 or greater.

Accordingly, basic amino acids include, but are not limited to, arginine, lysine, citrullene, ornithine, creatine, histidine, diaminobutanoic acid, diaminoproprionic acid, salts thereof or combinations thereof. In a particular embodiment, the basic amino acids are selected from arginine, citrullene, and ornithine.

In certain embodiments, the basic amino acid is arginine, for example, l-arginine, or a salt thereof.

In some embodiments the basic amino acid comprises at least one intermediate produced in the arginine deiminase system. The intermediates produced in the arginine deiminase system may be useful in an oral care composition to provide plaque neutralization for caries control and/or prevention. Arginine is a natural basic amino acid that may be found in the oral cavity. Arginine in the mouth may be utilized by certain dental plaque bacterial strains such as S. sanguis, S. gordonii, S. parasanguis, S. rattus, S. milleri, S. anginosus, S. faecalis, A. naeslundii, A. odonolyticus, L. cellobiosus, L. brevis, L. fermenium, P. gingivalis, and T. denticola for their survival. Such organisms may perish in an acidic environment that may be present at areas close to the tooth surface where acidogenic and aciduric cariogenic strains may use sugars to produce organic acids. Thus, these arginolytic strains may break down arginine to ammonia to provide alkalinity to survive and, in addition, buffer the plaque and make a hostile environment for the cariogenic systems.

Such arginolytic organisms may catabolize arginine by an internal cellular enzyme pathway system called the "arginine deiminase system" whereby intermediates in the pathway are formed. In this pathway, L-arginine may be broken down to L-citrulline and ammonia by arginine deiminase. L-citrulline may then be broken down by ornithane trancarbamylase in the presence of inorganic phosphate to L-ornithine and carbamyl phosphate. Carbamate kinase may then break down carbamyl phosphate to form another molecule of ammonia and carbon dioxide, and in the process also forms ATP (adenosine 5'-triphosphate). ATP may be used by the arginolytic bacteria as an energy source for growth. Accordingly, when utilized, the arginine deiminase system may yield two molecules of ammonia.

It has been found that, in some embodiments, the ammonia may help in neutralizing oral plaque pH to control and/or prevent dental caries.

The oral care composition of some embodiments of the present invention may include intermediates produced in the arginine deiminase system. Such intermediates may include citrulline, ornithine, and carbamyl phosphate. In some embodiments, the other care composition includes citrulline. In some embodiments, the oral care composition includes ornithine. In some embodiments, the oral care composition includes carbamyl phosphate. In other embodiments, the oral care composition includes any combination of citrulline, ornithine, carbamyl phosphate, and/or other intermediates produced by the arginine deiminase system.

The oral care composition may include the above described intermediates in an effective amount. In some embodiments, the oral care composition includes about 1 mmol/L to about 10 mmol/L intermediate. In other embodiments, the oral care composition includes about 3 mmol/L to about 7 mmol/L intermediate. In other embodiments, the oral care composition includes about 5 mmol/L intermediate.

The compositions of the invention are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

In various embodiments, the basic amino acid is present in an amount of about 0.5 wt. % to about 20 wt. % of the total composition weight, about 1 wt. % to about 15 wt. % of the total composition weight, for example about 1.5 wt. %, about 3.75 wt. %, about 5 wt. %, or about 7.5 wt. %, or about 10 wt % of the total composition weight.

Inorganic Acids, Inorganic Oxoacids, and Their Salts

The term "inorganic acid" refers to acids which do not contain carbon, e.g., mineral acids, e.g., hydrochloric acid. In a particular embodiment, the inorganic acid is an "inorganic oxoacid", which refers to acids, such as phosphoric acid or sulfuric acid, which contain oxygen and at least one other element, which have at least one hydrogen atom bound to oxygen, which form an ion by loss of one or more protons, and which do not contain carbon.

In certain embodiments, the Compositions of the Invention are substantially free of organic phosphates, e.g., alkyl phosphates or phytates and/or are substantially free of carbonates or bicarbonates. By "substantially free" is meant, in this context, present if at all in amounts of less than 5%, e.g., less than 1% relative to the inorganic acid or inorganic oxoacid.

Inorganic oxoacids within the scope of the present invention include, but are not limited to, sulfuric acid, phosphoric acid (i.e., orthophosphoric acid or $H_3PO_4$) and condensates of phosphoric acid, e.g., pyrophosphoric acid or tri-poly phosphoric acid. In some embodiments, the acid to form a salt with the basic amino acid or with the calcium is provided in the form of another salt, Salts thereof for use in the present invention to neutralize the basic amino acid are those having relatively high solubility, e.g., alkali salts and ammonium salts of orthophosphoric acid, such as potassium, sodium or ammonium orthophosphate, which are capable of buffering the basic amino acid to a pH of below about 7.5.

The oxoacids are present in an amount to neutralize the calcium and the basic amino acid sufficiently so as to provide an approximately neutral pH, e.g., pH about 6.8 to about 7.2.

In a particular embodiment, the oxoacid which provides the anion for the calcium salt and the oxoacid which provides the anion for the salt of the basic amino acid are the same, as the common ion effect is believed to lend stability to the formulation.

Fluoride Ion Source

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof.

In certain embodiments, the oral care composition of the invention may also contain a source of fluoride ions or fluorine-providing ingredient in amounts sufficient to supply about 25 ppm to 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A mouthwash, for example, would typically have about 100 to about 250 ppm fluoride. A toothpaste for general consumer use would typically have about 1000 to about 1500 ppm, with pediatric toothpaste having somewhat less. A dentifrice or coating for professional application could have as much as 5,000 or even 25,000 ppm fluoride.

Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Particulates and Abrasives

The Compositions of the Invention may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. Alternatively calcium carbonate, and in particular precipitated calcium carbonate, may be employed as an abrasive.

The compositions may include one or more additional particulate materials, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co. Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In certain embodiments, abrasive materials useful in the practice of the oral care compositions in accordance with the invention include silica gels and precipitated amorphous silica having an oil absorption value of less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the particulate or abrasive materials comprise a large fraction of very small particles, e.g., having a d50 less than about 5 microns for example small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

In some embodiments the basic amino acid is incorporated into a dentifrice composition having a base formulation comprising calcium carbonate, and in particular precipitated calcium carbonate, as an abrasive. L-arginine and arginine salts such as arginine bicarbonate are themselves distinctly bitter in taste, and in aqueous solution can also impart a fishy taste. Consequently, it was expected that when L-arginine or arginine salts were incorporated into oral care products such as dentifrice formulations at effective concentrations to impart anticavity efficacy and sensitivity relief, typically in an amount of from 2 to 10 wt % based on the total weight of the dentifrice formulation, the taste and mouthfeel of the dentifrice formulations would be degraded as compared to the same formulation without the addition of L-arginine or arginine salts.

However, it has surprisingly been found in accordance with this aspect of the present invention that the addition of L-arginine or arginine salts to a base dentifrice formulation comprising calcium carbonate can provide a significant enhancement of taste and mouthfeel attributes to the dentifrice formulation and to an increase in the overall acceptance of the product to a consumer.

Agents to Increase the Amount of Foaming

The oral care compositions of the invention also may include an agent to increase the amount of foam that is produced when the oral cavity is brushed.

Illustrative examples of agents that increase the amount of foam include, but are not limited to polyoxyethylene and certain polymers including, but not limited to, alginate polymers.

The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants

Another agent optionally included in the oral care composition of the invention is a surfactant or a mixture of compatible surfactants. Suitable surfactants are those which are reasonably stable throughout a wide pH range, for example, anionic, cationic, nonionic or zwitterionic surfactants.

Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference.

In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof.

Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

In a particular embodiment, the Composition of the Invention comprises an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon lemon, lime, grapefruit, and orange. Also useful are such chemicals as menthol, carvone, and anethole. Certain embodiments employ the oils of peppermint and spearmint.

The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

Chelating Agents

The oral care compositions of the invention also may optionally include one or more chelating agents able to complex calcium found in the cell walls of the bacteria. Binding of this calcium weakens the bacterial cell wall and augments bacterial lysis.

Another group of agents suitable for use as chelating agents in the present invention are the soluble pyrophosphates. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

Polymers

The oral care compositions of the invention also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether(methoxyethylene) having a molecular weight (M.W.) of about 30,000 to about 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. No. 4,992,420; U.S. Pat. No. 4,355,022; U.S. Pat. No. 4,154,815; U.S. Pat. No. 4,058,595; U.S. Pat. No. 3,991,177; and U.S. Pat. No. 3,696,191 all incorporated herein by reference. An enzyme of a mixture of several compatible enzymes in the current invention constitutes about 0.002% to about 2% in one embodiment or about 0.05% to about 1.5% in another embodiment or in yet another embodiment about 0.1% to about 0.5%.

Water

Water may also be present in the oral compositions of the invention. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition.

Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Methods of Manufacture

The compositions of the present invention can be made using methods which are common in the oral product area.

In one illustrative embodiment, the oral care composition is made by Method 2, described above. e.g., neutralizing arginine in a gel phase with phosphoric acid and mixing to form Premix 1.

Actives such as, for example, vitamins, CPC, fluoride, abrasives, and any other desired active ingredients are added to Premix 1 and mixed to form Premix 2.

A toothpaste base, for example, dicalcium phosphate is added to Premix 2 and mixed. The final slurry is formed into an oral care product.

Composition Use

The present invention in its method aspect involves applying to the oral cavity a safe and effective amount of the compositions described herein.

The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline.

Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

The Compositions of the Invention are thus useful in a method to reduce early enamel lesions (as measured by QLF or ECM) relative to a composition lacking effective amounts of fluorine and/or arginine.

The Compositions of the invention are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least about pH 5.5 following sugar challenge, reduce plaque accumulation, treat dry mouth, and/or clean the teeth and oral cavity.

Finally, by increasing the pH in the mouth and discouraging pathogenic bacteria, the Compositions of the Invention are useful to promote healing of sores or cuts in the mouth.

The compositions and methods according to the invention can be incorporated into oral compositions for the care of the mouth and teeth such as toothpastes, transparent pastes, gels, mouth rinses, sprays and chewing gum.

Enhancing oral health also provides benefits in systemic health, as the oral tissues can be gateways for systemic infections. Good oral health is associated with systemic health, including cardiovascular health. The compositions and methods of the invention provide particular benefits because basic amino acids, especially arginine, are sources of nitrogen which supply NO synthesis pathways and thus enhance microcirculation in the oral tissues. Providing a less acidic oral environment is also helpful in reducing gastric distress and creates an environment less favorable to Heliobacter, which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1—Stability Test of Arginine Bicarbonate Formulation

When arginine bicarbonate is placed in a pH neutral dicalcium base toothpaste formulation, it is found to be not stable, as the bicarbonate degrades to carbon dioxide, leading to bloating and busting of the toothpaste tubes:

| Product | Initial Cosmetic | 12 weeks accelerated (40° C.) |
|---|---|---|
| Dical + 2.0% arginine-bicarbonate | OK | Severe bloating, tubes burst |
| Dical + 3.75% L-arginine | OK | OK |

Dical = Dicalcium phosphate dihydrate

Example 2—Fluoride Stability

As is seen in the following table, simply adding arginine to a dicalcium phosphate/fluoride base and adjusting to neutral pH results in poor fluoride stability, with fluoride dropping off to sub-effective levels within a few weeks. We have surprisingly discovered that neutralization of arginine in the gel phase with phosphoric acid prior to addition of dicalcium phosphate dihydrate abrasive results in increased fluoride stability.

| Product | Initial Fluoride | 4 weeks (40° C.) | 8 weeks (40° C.) | 12 weeks (40° C.) |
|---|---|---|---|---|
| Dical + 1.5% L-arginine | 1442 ppm | 1049 ppm | 693 ppm | 366 ppm |
| Dical + 3.75% L-arginine | 953 ppm | 812 ppm | 680 ppm | 51 ppm |
| Dical + 1.5% L-arginine + 0.6% $H_3PO_4$ | 1516 ppm | 1372 ppm | 1325 ppm | 1208 ppm |
| Dical + 3.75% L-arginine + 1.25% $H_3PO_4$ | 1489 ppm | 1319 ppm | 1294 ppm | 1138 ppm |

Notes:
Dical = Dicalcium phosphate dihydrate

Phosphoric acid is provided as 85% solution

The degree of neutralization of the arginine with the acid is related maintaining fluoride stability, with either too little or too much resulting in some loss of stability as seen in the following study:

| Product | Initial Fluoride | 4 weeks (40° C.) | 8 weeks (40° C.) | 12 weeks (40° C.) |
|---|---|---|---|---|
| Dical + 1.5% L-arginine + 0.5% $H_3PO_4$ | 1419 ppm | 1335 ppm | 1269 ppm | 1107 ppm |
| Dical + 1.5% L-arginine + 0.6% $H_3PO_4$ | 1516 ppm | 1372 ppm | 1325 ppm | 1208 ppm |
| Dical + 1.5% L-arginine + 0.75% $H_3PO_4$ | 1439 ppm | 1264 ppm | 1184 ppm | 1029 ppm |
| Dical + 3.75% L-arginine + 1.0% $H_3PO_4$ | 1356 ppm | 1098 ppm | 882 ppm | 634 ppm |
| Dical + 3.75% L-arginine + 1.25% $H_3PO_4$ | 1489 ppm | 1319 ppm | 1294 ppm | 1138 ppm |
| Dical + 3.75% L-arginine + 1.45% $H_3PO_4$ | 1385 ppm | 1219 ppm | 1117 ppm | 958 ppm |

Notes:
Dical = Dicalcium phosphate dihydrate

Fluoride supplied as sodium monofluorophosphate, units in ppm fluoride Optimally, the ratio of arginine to phosphoric acid for optimal fluoride stability is thus approximately 2:1 to approximately 4:1, e.g., from about 2.5:1 to 3:1, e.g., 1.5% arginine to 0.6% phosphoric acid or 3.75% arginine to 1.25% phosphoric acid (with phosphoric acid as 85% solution) The optimal ratio for a given formulation may vary somewhat however depending on the other ingredients in the particular formulation.

Example 3: Formulation

An optimized arginine/calcium/fluoride toothpaste formulation is prepared using the following ingredients:

| MATERIAL | WEIGHT % |
|---|---|
| Deionized Water | 21.479 |
| Glycerin | 22.000 |
| Carboxymethyl cellulose | 1.100 |
| Sodium Saccharin | 0.200 |

-continued

| MATERIAL | WEIGHT % |
|---|---|
| Sodium Monofluorophosphate | 1.100 |
| Tetrasodium pyrophosphate | 0.500 |
| Phosphoric acid 85% | 0.600 |
| L-Arginine | 1.500 |
| Dicalcium phosphate dihydrate | 46.500 |
| Sodium lauryl sulfate 35% | 4.071 |
| Flavor | 0.950 |
| TOTAL | 100.000 |

This formulation demonstrates good shelf life, cosmetic stability and fluoride stability.

Example 4—Efficacy in Remineralization

The neutralized dicalcium phosphate/arginine phosphate/fluoride formulation is tested against dicalcium phosphate/fluoride formulations without arginine in a clinical study of demineralization/remineralization.

In this model enamel specimens experience conditions of demineralization and remineralization in the mouth. Demineralizing conditions are created by dipping the specimens in s sugar solution. The cariogenic bacteria form acids and cause the pH to drop. In this model, blocks of bovine specimens that have been polished flat to a mirror finish are prepared. A micro hardness tester is used to measure the hardness of the enamel specimen at baseline (M1). The micro hardness tester uses a diamond tipped probe to create an indent in the enamel specimen with a known and constant load. The length of the indent is inversely related to the enamel hardness. Enamel hardness is directly correlated with the mineral content. The specimens are covered with a Dacron mesh and then mounted in a retainer. The specimens are worn 24 hours per day for 5 days. During the 5 day period, the panelists dip their retainer in a sucrose solution 4 times per day. This treatment causes the pH fluctuations. The panelists brush their teeth two times per day with the assigned dentifrice while the retainer is in the mouth. After 5 days, the specimens are removes from the retainer and a micro hardness measurement is conducted (M2). The plaque can be further analyzed for plaque ecology or plaque metabolism measurements. Because of the highly cariogenic condition created by dipping the specimens sugar 4 times per day, most treatments tend to experience a net loss in mineral after the 5 day treatment, hence, the name "demin-remin model". The best treatment loses the least amount of mineral. There are circumstances, however, where a net increase in hardness is achieved with a particularly effective treatment.

The statistical analysis is a two factor analysis using the subject and treatment as factors. The results can be expressed as a % change in hardness (M2−M1)/M1×100 or a net change in hardness M2−M1. If a percent change is used as the measured response, a two factor ANOVA is conducted. If a net change in hardness is used, a two factor ANCOVA is conducted using M1 as the covariate. Differences are considered significant if a 95% confidence level is achieved. Typically a 250 ppm fluoride (or nonfluoride) and a dentifrice with a standard level of fluoride are included as negative and positive controls and are used to validate the model. The fluoride level in the positive control is most commonly 1000, 1100, or 1450 ppm fluoride. The control chosen is dependent on the fluoride level in the test dentifrice. The model is considered validated if positive control is shown to be significantly better than the negative control. Once the model is validated, the test product is compared to the negative control. It should be noted that the panelist effect is normally very significant; therefore, it is not expected that the same numerical result for an identical treatment will be obtained using a different study population.

| Formulation | % mineral change |
|---|---|
| Dical + 250 MFP | −12.7 |
| Dical + 1450 MFP | −1.87 |
| Dical + 1.5% neutralized arginine + 1450 MFP (Example 3) | +8.27 |

Notes:
Dical = Dicalcium phosphate dihydrate
MFP = sodium monofluorophosphate, units in ppm fluoride The neutralized dicalcium phosphate/arginine phosphate/fluoride formulation is the only formulation to show an actual increase mineralization in this clinical study.

Example 5—Efficacy in Raising Plaque pH

Plaque ammonia production in patients using the formulation of example 3 is compared to a formulation which does not have arginine. Plaque is collected from patients in the clinical study of the previous example after one week of usage of the different formulations, and concentration of the samples is normalized in buffer. The samples are challenged with sucrose, then arginine is added. The plaque is incubated at 37 degrees C. for 30 minutes, and ammonia production measured using a commercially available ammonia detection kit from Diagnostic Chemicals Limited (Oxford, Conn.) to measure ammonia production.

| Formulation | Ammonia levels (ppm) |
|---|---|
| Dical + 250 MFP | 1.97 |
| Dical + 1450 MFP | 1.79 |
| Dical + 1.5% neutralized arginine + 1450 MFP (Example 3) | 2.77 |

Notes:
Dical = Dicalcium phosphate dihydrate
MFP = sodium monofluorophosphate, units in ppm fluoride After one week of usage, the formulation of example 3 results in a plaque which has significantly higher levels of ammonia, showing that it contains relatively higher levels of arginolytic bacteria.

This result is confirmed by measuring the plaque pH directly. Plaque is collected from the subjects in the morning after a period of fasting and no brushing, at the baseline, first, second, third and fourth weeks of the trial. The buccal and lingual surfaces are swabbed. The sample concentrations are normalized in buffer. The samples are challenged with sucrose, then incubated at 37 degrees C. for two hours, after which time the pH is measured to determine plaque pH. After four weeks, the plaque pH of the arginine group is between 5.5 and 5.6, while that of the control group is about 5.3, essentially unchanged from baseline. This result is statistically and clinically relevant, because enamel exposed to pH below 5.5 is subject to demineralization and damage.

Accordingly, the arginine toothpaste with fluoride is seen to provide a long term buffering effect in the plaque, which persists for long periods after brushing, and which helps protect the teeth and control cariogenic bacteria, notwithstanding that the arginine itself has been neutralized in the formulation with phosphoric acid.

Example 6—Efficacy in Reducing Bacterial Attachment

Toothpaste formulations are provided as follows (amounts given as weight percent of final formulation):

| Ingredients | Formulation A | Formulation B | Control |
|---|---|---|---|
| Glycerin | 22 | 22 | 22 |
| Sodium CMC-7MF | 1 | 0.85 | 1 |
| Tetrasodium phosphate | 0.25 | 0.25 | 0.25 |
| Water | 18.14 | 15.3 | 24.94 |
| L-Arginine | 5 | 5 | 0 |
| Phosphoric acid | 1.8 | 1.8 | 0 |
| Sodium MFP | 0.76 | 0.76 | 0.76 |
| Sodium Saccharin | 0.2 | 0.2 | 0.2 |
| Dicalcium phosphate dihydrate | 48.76 | 48.76 | 48.76 |
| Flavor | 0.89 | 0.89 | 0.89 |
| Sodium Lauryl Sulfate | 1.2 | 0 | 1.2 |
| Cocamidopropyl betaine | 0 | 1.34 | 0 |
| Polysorbate 20 | 0 | 1.68 | 0 |
| Pluronic F127 | 0 | 1.17 | 0 |
| Total (%) | 100 | 100 | 100 |

The above formulations are tested in vitro in an artificial mouth model designed to measure bacterial attachment to toothpaste-treated hydroxyapatite (HAP) disks over a 24 hour period, generally as described by Gaffar, A. et al. *American Journal of Dentistry*, vol. 3, September 1990. This test showed reductions of 27% for Formulation A and 10% for Formulation B compared to the control formulation, which did not contain arginine, suggesting that arginine and particularly arginine in combination with an anionic surfactant such as sodium lauryl sulfate, is useful for inhibiting bacterial attachment:

| | Formula A | Formula B | Solbrol formulation (positive control) | Control |
|---|---|---|---|---|
| Mean | 0.1418 | 0.1736 | 0.1327 | 0.1932 |
| SD | 0.0156 | 0.0357 | 0.0241 | 0.0401 |
| T Test vs. control (p value) | 0.00 | 0.32 | 0.00 | 1.00 |
| % reduction vs. control | 26.62 | 10.15 | 31.30 | 0.00 |

Example 7—Effect on Availability and Delivery of Antibacterial

Formulations are prepared using commercial toothpaste formulations comprising 0.3% by weight of triclosan and 0.243% by weight of sodium fluoride, to which is added 0, 1%, 3%, and 5% L-arginine hydrochloride (pH 7.0). Incorporation of L-arginine in the dentifrice enhances the amount of soluble triclosan available from the formulation, from about 70% to about 80% (1% arginine), 85% (3% arginine), and 95% (5% arginine).

The artificial mouth model described in the preceding example is used with the modification that the hydroxyapatite disks are treated with the dentifrice slurry before exposure to bacteria. It is shown that the incorporation of L-arginine into the Total® formulation enhances delivery of the triclosan to the disks by about 50%, with uptake at 30 minutes increasing from approximately 40 micrograms triclosan per disk for the control to about 60 micrograms triclosan for the 5% arginine formulation. After 24 hours, the control disk has retained about 10 micrograms per disk, compared to about 20 micrograms for the 5% arginine formulation, a significant enhancement. This leads directly to an enhancement of the antibacterial effect of the formulation, with a statistically significant reduction of about 15% in inihibition of growth of *A. viscosus*.

Example 8—Mouth Rinse Formulation

Mouth wash formulations of the invention are prepared using the following ingredients:
Arginine Rinse with Fluoride

| RAW MATERIAL | WEIGHT % |
|---|---|
| Deionized Water | 72.149 |
| Glycerin | 10.000 |
| 70% Sorbitol | 10.000 |
| 95% Ethanol | 6.000 |
| Polysorbate 20 | 1.000 |
| Sodium benzoate | 0.110 |
| Sodium fluoride | 0.050 |
| Sodium Sacharin | 0.020 |
| Cetylpyridinium chloride | 0.050 |
| Phosphoric acid 85% | 0.120 |
| L-Arginine | 0.300 |
| Flavor | 0.200 |
| Colorants | 0.001 |
| TOTAL | 100.000 |
| pH | 7.0 |

Example 9—Dentifrice Formulation Comprising Precipitated Calcium Carbonate (PCC)

A panel of consumer testers trained in testing the sensory attributes of dentifrice formulations was subjected to different dentifrice formulations which were used under double-blind consumer testing conditions replicating consumer use of dentifrice formulations.

The panel was asked to use the dentifrice formulations conventionally and then to rate various sensory characteristics. For a base dentifrice formulation comprising precipitated calcium carbonate (PCC), the known formulation acted as a placebo control, and corresponding formulations additionally comprising 1, 2, 3 or 5 wt % arginine bicarbonate were also tested. Surprisingly, it was found that the arginine bicarbonate-containing PCC formulations exhibited increases in consumer acceptance for flavor intensity, cooling and ease to foam attributes, and moreover the formulation additionally comprising 2 wt % arginine bicarbonate exlibited increases in overall liking, overall liking of taste, taste while brushing and taste after brushing. In addition, the formulations additionally comprising arginine bicarbonate were perceived as significantly better than the placebo control in all image attributes, including perceived efficacy, mouth/teeth feeling of clean, product suitability, taste and overall product quality.

In contrast, when formulations having dicalcium phosphate, rather than precipitated calcium carbonate (PCC), as the base were tested, the addition of arginine bicarbonate did not exhibit significantly improved sensory characteristics as compared to the same formulation without the addition of arginine bicarbonate.

The Example shows that the addition of a basic amino acid such as arginine, in particular as bicarbonate, can surprisingly enhance the sensory characteristics of dentifrice formulations, most particularly having a base formulation of precipitated calcium carbonate (PCC), when used in an oral care composition of the invention.

Example 10—Basic Amino Acids Other Than Arginine

An overnight culture of S. sanguis was grown at 37° C. in trypticase soy broth (Becton Dickinson, Sparks, Md.). The culture was centrifuged at 5,000 rpm for 5 minutes at 1 milliliter at a time into preweighed tubes in order to accumulate approximately 5 milligrams of wet pellet weight. The pellet was then resuspended into 20 millimolar potassium phosphate buffer (J T Baker, Phillipsburg, N.J.), pH 4.0, to simulate a stressed environment for the bacterial cell where ammonia would be produced for survival. The final concentration was 5 milligram per milliliter. To this final concentration, a 5 millimolar final concentration of L-arginine, L-citrulline, or L-ornithine was added along with a 0.1% final concentration of sucrose (VWR, West Chester, Pa.). This mixture was then incubated at 37° C. in a shaking water bath for 30 minutes before ammonia production was determined.

In order to analyze for ammonia, an Ammonia Assay kit was used from Diagnostic Chemicals Limited (Oxford, Conn.). The intended use of this specific kit is for the in vitro quantification of ammonia in plasma, but the procedure was modified in order to determine and quantify the ammonia production in plaque and/or bacteria.

The table below shows the ammonia production values from 6 separate trials using S. sanguis at pH 4.0 as described above. The results confirm that the intermediates produced by the arginine deiminase system can be used to produce ammonia for cell survival.

| Trial # | L-Arginine Ammonia (ppm) | L-Citrulline Ammonia (ppm) | L-Ornithine Ammonia (ppm) |
|---|---|---|---|
| 1 | 0.509 | 0.185 | 0.185 |
| 2 | 0.866 | 0.346 | 0.260 |
| 3 | 2.20 | 0.332 | 0.047 |
| 4 | 1.62 | 0.194 | 0.0 |
| 5 | 0.5 | 0.226 | 0.181 |
| 6 | 0.679 | 0.951 | 0.135 |
| Mean | 1.06 | 0.951 | 0.134 |

The Example shows that basic amino acids other than arginine are effective to produce ammonia within the oral cavity, and thus to increase plaque pH when used in a oral care composition of the invention.

The invention claimed is:

1. An oral care composition comprising
   a. an effective amount of arginine phosphate;
   b. an effective amount of sodium monofluorophosphate;
   c. a particulate material which has a pH in an unbuffered solution of less than about 7.5,
   wherein the particular material comprises dicalcium phosphate dihydrate;
   wherein the composition has a pH between 6.8 and 7.2; and
   wherein the composition is substantially free of organic phosphates.

2. A composition of claim 1 which is a dentifrice.

3. A composition of claim 1 further comprising an anionic surfactant.

4. A composition according to claim 3 wherein the anionic surfactant is sodium lauryl sulfate.

5. A composition of claim 1 further comprising an antibacterial agent.

6. A composition according to claim 5 wherein the antibacterial agent is zinc citrate.

7. A composition of claim 1 further comprising an anionic polymer.

8. A composition according to claim 7 wherein the anionic polymer is a copolymer of methyl vinyl ether and maleic anhydride.

9. A composition according to claim 1, wherein a radioactive dentin abrasion (RDA) of the composition is less than 150.

10. A composition according to claim 1 in the form of a toothpaste further comprising one or more of water, abrasives surfactants, foaming agents, vitamins, polymers, enzymes, humectants, thickeners, antimicrobial agents, preservatives, flavorings, colorings and/or combinations thereof.

11. A method comprising applying an effective amount of the oral composition of claim 1 to an oral cavity to a. reduce or inhibit formation of dental caries, b. reduce, repair or inhibit early enamel lesions, c. reduce or inhibit demineralization and promote remineralization of the teeth, d. reduce hypersensitivity of the teeth, e. reduce or inhibit gingivitis, f. promote healing of sores or cuts in the mouth, g. reduce levels of acid producing bacteria, h. increase relative levels of arginolytic bacteria, i. inhibit microbial biofilm formation in the oral cavity, j. raise and/or maintain plaque pH at levels of at least pH 5.5 following sugar challenge, k. reduce plaque accumulation, l. treat, relieve or reduce dry mouth, m. immunize the teeth against cariogenic bacteria, n. whiten teeth, o. reduce erosion, p. clean the teeth and oral cavity, and/or q. promote systemic health, including cardiovascular health.

12. The method of claim 11, wherein the applying is to reduce or inhibit formation of dental caries.

13. An oral care composition according to claim 1 wherein the arginine phosphate is present in an amount to provide from 0.1 to 20 wt % of arginine free base by weight of the total composition.

14. An oral care composition according to claim 1 wherein the arginine phosphate is present in an amount to provide from 1 to 15 wt % of arginine free base by weight of the total composition.

15. An oral care composition according to claim 1 wherein the soluble fluoride salt is present in an amount of from 0.01 to 2 wt % of the total composition weight.

16. An oral care composition according to claim 1 wherein the sodium monofluorophosphate is present in an amount to provide 50 to 25,000 ppm by weight of fluoride ions in the total composition weight.

17. An oral care composition according to claim 1 wherein the dicalcium phosphate dihydrate is present in an amount of from 15-70 wt % of the total composition weight.

18. A composition according to claim 6, wherein the zinc citrate is present in an amount of 0.01 to 5% by weight of the total composition.

* * * * *